US006754527B2

United States Patent
Stroebel et al.

(12) United States Patent
(10) Patent No.: US 6,754,527 B2
(45) Date of Patent: Jun. 22, 2004

(54) SYSTEM AND METHOD FOR REDUCING NOISE IN AN IMPLANTABLE MEDICAL DEVICE

(75) Inventors: John C. Stroebel, Blaine, MN (US); Forrest C. M. Pape, New Brighton, MN (US); Paul J. Huelskamp, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 300 days.

(21) Appl. No.: 09/948,069

(22) Filed: Sep. 6, 2001

(65) Prior Publication Data

US 2003/0045906 A1 Mar. 6, 2003

(51) Int. Cl.[7] .................................................. A61N 1/39
(52) U.S. Cl. ........................................... 607/5; 128/901
(58) Field of Search ............................. 607/2, 5, 7, 60; 128/901

(56) References Cited

U.S. PATENT DOCUMENTS 5,083,562 A    1/1992  de Coriolis et al.
5,473,526 A   12/1995  Svensson et al.
5,488,553 A    1/1996  Renger
6,076,018 A    6/2000  Sturman et al.
6,171,252 B1 * 1/2001  Roberts ....................... 600/485

* cited by examiner

Primary Examiner—Kennedy Schaetzle
(74) Attorney, Agent, or Firm—Girma Wolde-Michael; Michael C. Soldner

(57) ABSTRACT

A system and method for reducing the amount of noise causes by inductive elements within an implantable medical device. In particular, the invention provides a system for gradually initiating and terminating the current flow within inductive elements such as transformers that are used to charge energy storage devices such as high-voltage capacitors of an implantable cardio/defibrillator. This more gradual change in the rate of current flow prevents ground shifts and subsequent noise spikes within the device. This, in turn, allows cardiac signals to be sensed more accurately by sensing circuits, preventing oversensing, and minimizing the occurrence of inappropriate shock delivery.

25 Claims, 4 Drawing Sheets

SYSTEM AND METHOD FOR REDUCING NOISE IN AN IMPLANTABLE MEDICAL DEVICE

FIELD

The invention relates to a system and method for reducing noise in an implantable medical device; and, more specifically, relates to reducing noise during charging of high-voltage capacitors to prevent oversensing.

BACKGROUND

In some implanted devices, sources of noise are generated internally that may interfere with sensing of signals. Some implanted devices that deliver high-voltage shocks such as Implantable Cardioverter/Defibrillators (ICDs), for example, include inductive elements such as transformers. These inductive elements may be used to charge capacitors in preparation of high-voltage shock delivery.

To perform charging of the capacitors, current is made to flow through the transformer. When current flow is abruptly enabled or disabled, as is the case in prior art implantable medical devices (IMDs), a shift in the ground plane voltage level occurs, causing a noise spike. This noise spike may adversely affect the operation of various circuits within the IMD.

One type of circuit that is particularly impacted by noise generation includes the amplifier circuits used to sense electrical signals in a patient's body. These amplifiers are used to sense electrocardiogram (EGM) signals in the atrial and ventricular chambers of the heart. In one instance, an EGM signal may be received by an IMD and analyzed to determine the presence of an arrhythmia such as a tachyarrhythmia or a fibrillation. This type of determination is made by detecting heart rate and/or the morphology of the cardiac signal. If an arrhythmia is detected, the IMD may select and deliver appropriate therapy, which may include anti-tachy pacing (ATP), or a high-voltage shock. Noise induced in the amplifier circuits may lead to oversensing of R and P waves, and may result in the delivery of inappropriate therapy, including painful high-voltage shocks.

One particular problematic situation involves attempting to sense cardiac signals at the same time charging of the high-voltage capacitors is being initiated in preparation for shock delivery. This may occur, for example, after the system sensed the presence of an arrhythmia, then responded by delivering ATP therapy. As is known in the art, this type of therapy may be followed by delivery of a high-voltage shock in the event the arrhythmia was not terminated by the ATP therapy. To ensure the shock may be delivered as soon as possible to prevent patient syncope, many systems begin charging high-voltage capacitors in preparing for the shock delivery at the same time the system is sensing the cardiac signals to determine whether the arrhythmia has terminated. Noise induced in the amplifier circuits by the capacitor charging operation may prevent an accurate assessment of the cardiac signal, leading to inappropriate shock delivery.

Prior art IMDs have generally prevented the foregoing situation by beginning signal sensing to detect the termination of an arrhythmia only after the cessation of capacitor charging. However, the detection process requires several cardiac cycles to complete, and can be more accurate if more cardiac cycles are available for analysis. Ideally, cardiac cycles both during and after capacitor charging would be available for analysis to detect the termination of the arrhythmia.

What is needed, therefore, is a circuit that reduces the amount of noise generated by inductive elements within an IMD. Ideally, the circuit would reduce the noise levels in the amplifier circuits so that more accurate analysis of arrhythmia termination may be performed, and fewer inappropriate shocks are delivered.

SUMMARY

The invention is directed to a system and method for reducing the amount of noise causes by inductive elements within an implantable medical device. In particular, the invention provides a system for gradually stopping and starting the current flow within the inductive elements such as transformers that are used to charge energy storage devices such as high-voltage capacitors of an implantable cardioverter/defibrillator (ICD). This more gradual change in the rate of current flow prevents ground shifts and subsequent noise spikes within the device. This, in turn, allows cardiac signals to be sensed more accurately, preventing oversensing, and minimizing the occurrence of inappropriate shock delivery.

According to one embodiment of the invention, starting and stopping of current flow during capacitor charging is accomplished using a pulsed signal having a substantially fixed frequency and a variable duty cycle. The duty cycle is varied to gradually increase current flow to initiate capacitor charging. After charging is completed, current flow is gradually reduced by decreasing the duty cycle. In an alternative embodiment, the duty cycle may be substantially constant, with the pulse frequency being varied to increase, then decrease, current flow for capacitor charging. In still another embodiment, both duty cycle and pulse frequency may be varied.

According to another aspect of the invention, the charging of the capacitors may be interrupted at predetermined intervals to allow data communications to occur between the IMD and an external device. The circuit associated with charging of the high-voltage capacitors generates electromagnetic interference that can cause data errors during communication transmissions between the IMD and an external device such as programmer. To minimize this interference, the charging circuit may be periodically disabled during the charging process so that communications may occur. These periodic interruptions in the charging are used to initiate data communications with external devices that may be completed during one or more such interruptions.

The system according to one embodiment of the invention includes a charge storage device such as a capacitor, and a charging circuit that stores energy on the charge storage device. The charging circuit has both an enabled state and a disabled state. A control circuit coupled to the charging circuit causes the charging circuit to transition from the disabled state to the enabled state over a period of time in a gradual manner so that noise spikes are not generated. A similar mechanism is utilized to disable the charging operation.

According to another embodiment of the invention, the system includes an energy storage device, and a charging circuit coupled to store charge on the energy storage device. A control circuit is coupled to the charging circuit to cause the charging circuit to store charge at a varying charge rate, such as a gradually increasing, or a gradually decreasing rate.

Another embodiment of the invention is a method that includes the step of initiating storing of a charge on a charge storage device included within an IMD. The method further includes controlling the rate of the storing of the charge in a manner that maintains the ground plane of the IMD at a substantially constant voltage potential.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
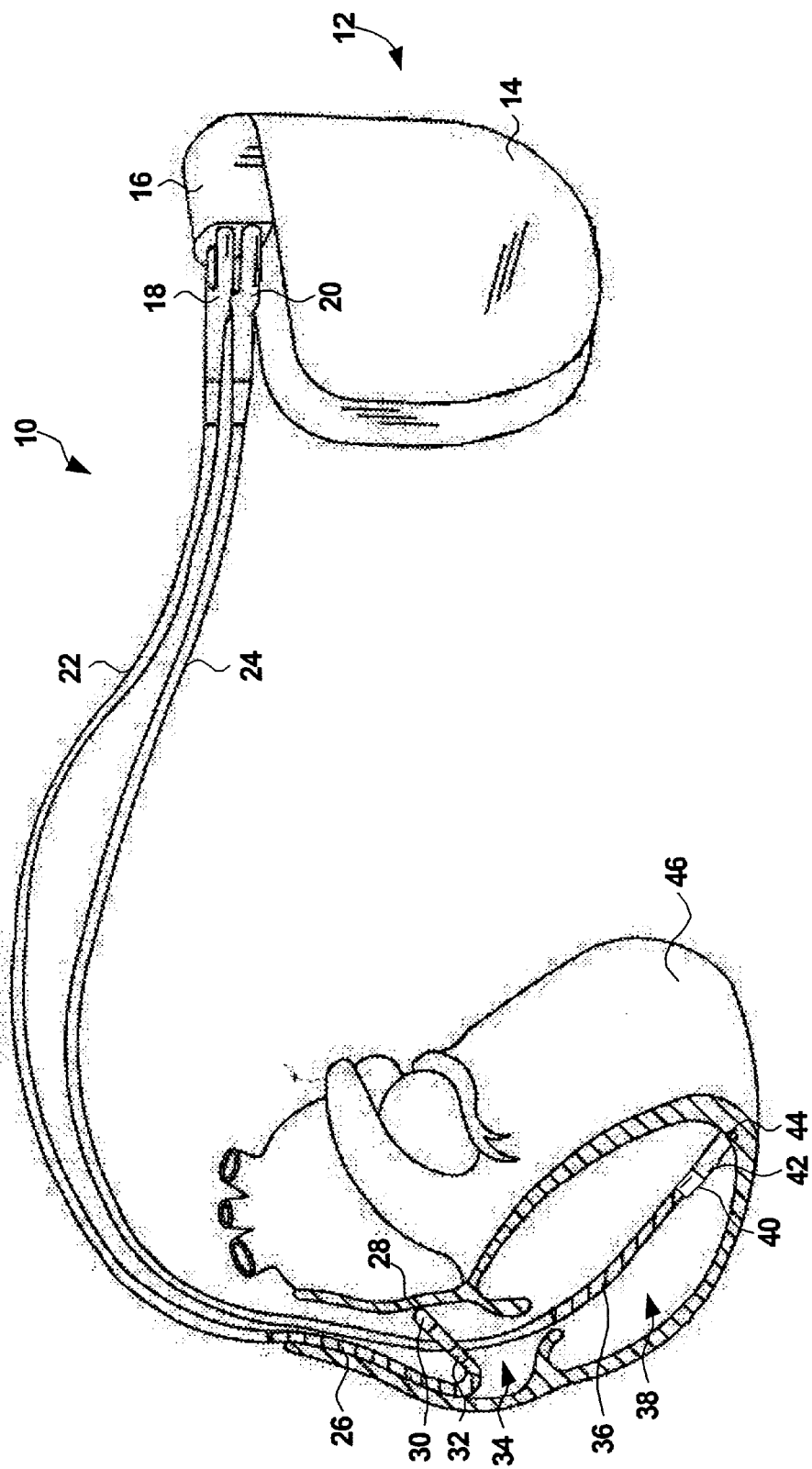
FIG. 1 is a diagram illustrating an implantable defibrillator and lead system in which the invention may be practiced.

FIG. 1 illustrates an example implanted defibrillator and lead system 10 in which the present invention may be practiced. It will be understood that the invention is not limited to the exemplary device or system shown in FIG. 1, but may be practiced in a wide variety of device implementations.

System 10, which is shown in associated with a human heart 46, comprises a ventricular lead, which includes elongated insulative lead body 24. The lead body may carry three coiled or cable conductors according to any of the lead designs known in the art. The distal end of the ventricular lead is deployed in right ventricle 38. Located adjacent the distal end of the ventricular lead are ring electrode 40, extendable helix electrode 44, mounted retractably within insulative electrode head 42, and elongated (approximately 5 cm) defibrillation coil electrode 36. Defibrillation electrode 36 may be fabricated from many materials, such as platinum or platinum alloy. Each of the electrodes is coupled to a respective one of the conductors within lead body 24.

Electrodes 40 and 44 are employed for cardiac pacing and for sensing ventricular depolarizations. Accordingly, electrodes 40 and 44 serve as sensors for sensing an electrocardiogram (EGM) signal. At the proximal end of the ventricular lead is bifurcated connector 20 that carries three electrical connectors, each coupled to one of the lead conductors.

The atrial/superior vena cava (SVC) lead includes elongated insulative lead body 22, and may carry three conductors in a manner similar to that discussed above. These conductors may be concentrically coiled and separated from one another by tubular insulative sheaths, or may be configured in any of the other ways known in the art. The distal end of the atrial/SVC lead is deployed in right atrium 34. Located adjacent the distal end of the atrial/SVC lead are ring electrode 32 and extendable helix electrode 28, mounted retractably within insulative electrode head 30. Each of the electrodes is coupled to one of the conductors within lead body 22. Electrodes 28 and 32 are employed for atrial pacing and for sensing atrial depolarizations. Accordingly, electrodes 28 and 32 serve as sensors for an A-EGM.

Elongated coil electrode 26 is provided proximal to electrode 32 and coupled to the third conductor within the lead body 22. Electrode 26 preferably is 10 cm in length or greater and is configured to extend from the SVC toward the tricuspid valve. At the proximal end of the lead is a bifurcated connector 18, which carries three electrical connectors, each coupled to one of the lead conductors.

Implantable ICD 12 is shown in combination with the leads, with lead connector assemblies 18 and 20 inserted into connector block 16. Optionally, insulation of the outward facing portion of housing 14 of ICD 12 may be provided using a plastic coating such as parylene or silicone rubber, as is employed in some unipolar cardiac pacemakers. However, the outward facing portion may instead be left uninsulated, or some other division between insulated and uninsulated portions may be employed. The uninsulated portion of the housing 14 optionally serves as a subcutaneous defibrillation electrode, used to defibrillate either the atria or ventricles.

As described in detail below, ICD 14 includes a charging circuit that stores energy for producing defibrillation pulses, which are delivered to the patient via electrode 26 or electrode 36. When the charging circuit is storing energy, the charging circuit generates electromagnetic noise that could interfere with sensing cardiac signals. As a result, oversensing may occur. The current invention minimizes the noise generated by the charging circuit by gradually enabling and disabling the charging of the high-voltage capacitors in a manner to be discussed below.

Figure 2:
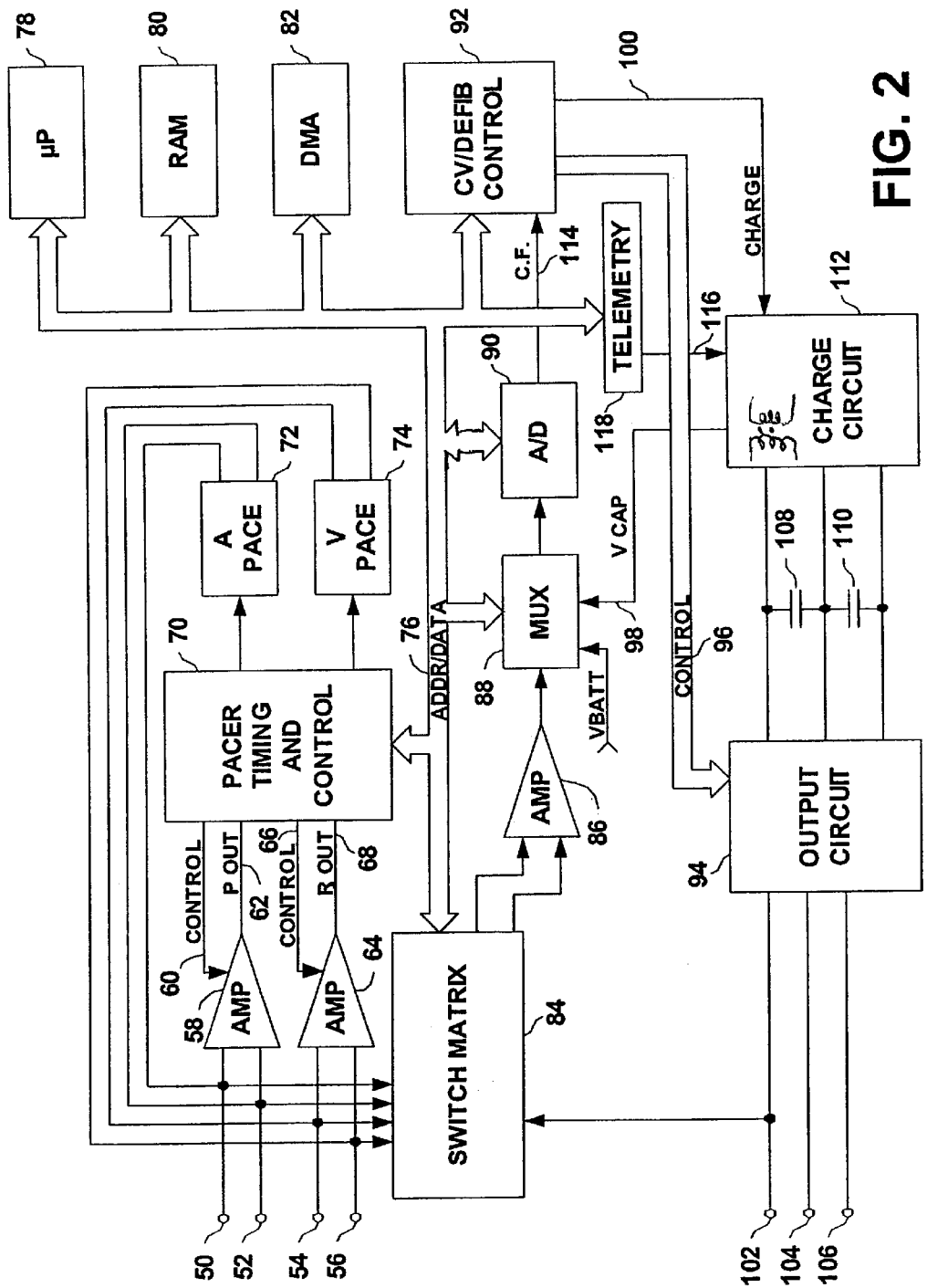
FIG. 2 is a functional schematic diagram of an implantable ICD in which the invention may be practiced.

FIG. 2 is a functional schematic diagram of an ICD, in which the present invention may be practiced. FIG. 2 should be taken as exemplary of one type of device in which the invention may be embodied, and is only one possible functional representation of system 10 shown in FIG. 1. It will be understood that the invention may be practiced in a system that includes more or fewer features than are depicted in FIG. 2.

The device illustrated in FIG. 2 is provided with an electrode system including electrodes as illustrated in FIG. 1. For clarity of analysis, the pacing/sensing electrodes 50, 52, 54 and 56 are shown as logically separate from pacing/defibrillation electrodes 102, 104 and 106.

Electrodes 102, 104 and 106 correspond to an atrial defibrillation electrode, a ventricular defibrillation electrode and the uninsulated portion of the housing of the ICD. Electrodes 102, 104 and 106 are coupled to high-voltage output circuit 94. High voltage output circuit 94 includes high voltage switches controlled by cardioversion/defibrillation (CV/defib) control logic 92 via control bus 96. The switches within output circuit 94 control which electrodes are employed and which are coupled to the positive and negative terminals of the capacitor bank including capacitors 108 and 110 during delivery of the defibrillation pulses.

Electrodes 54 and 56 are located on or in the ventricle and are coupled to R-wave sense amplifier 64. Operation of amplifier 64 is controlled by pacer timing/control circuitry 70 via control lines 66. Amplifier 64 performs functions in addition to amplification, such as filtering the signals sensed by electrodes 54 and 56. Amplifier 64 also includes a comparator that compares the input signal to a pre-selected ventricular sense threshold. A signal is generated on R-out line 68 whenever the signal sensed between electrodes 54 and 56 exceeds the ventricular sense threshold.

Electrodes 50 and 52 are located on or in the atrium and are coupled to P-wave sense amplifier 58. Operation of amplifier 58 is controlled by pacing circuitry 70 via control lines 60. Amplifier 58 performs functions in addition to amplification, such as filtering the signals sensed by electrodes 50 and 52. Amplifier 58 includes a comparator that compares the input signal to a pre-selected atrial sense threshold, which is usually different from the ventricular sense threshold. A signal is generated on P-out line 62 whenever the signal sensed between electrodes 50 and 52 exceeds the atrial sense threshold.

Switch matrix 84 is used to select which of the available electrodes are coupled to wide band (2.5–100 Hz) amplifier 86 for use in signal analysis. Signal analysis may be performed using analog circuitry, digital circuitry or a combination of both.

Selection of electrodes is controlled by the microprocessor 78 via data/address bus 76. The selection of electrodes may be varied as desired. Signals from the electrodes selected for coupling to band-pass amplifier 86 are provided to multiplexer 88, and thereafter converted to multi-bit digital signals by analog-to-digital (A/D) converter 90, for storage in random access memory (RAM) 80 under control of direct memory access circuit 82.

Much of the circuitry in FIG. 2 is dedicated to the provision of arrhythmia management therapies, including cardiac pacing, cardioversion and defibrillation therapies. An exemplary apparatus comprises pacer timing/control circuitry 70, which includes programmable digital counters that control the basic time intervals associated with DDD, VVI, DVI, VDD, AAI, DDI and other modes of single- and dual-chamber pacing. Pacing circuitry 70 also controls escape intervals associated with anti-tachyarrhythmia pacing in both the atrium and the ventricle, employing any of a number of anti-tachyarrhythmia pacing therapies.

Intervals defined by pacing circuitry 70 include atrial and ventricular pacing escape intervals, the refractory periods during which sensed P-waves and R-waves are ineffective to restart timing of the escape intervals, and the pulse widths of the pacing pulses. The durations of these intervals are determined by microprocessor 78, in response to stored data in memory 80 and are communicated to pacing circuitry 70 via address/data bus 76. Pacing circuitry 70 also determines the amplitude of the cardiac pacing pulses under control of microprocessor 78.

During pacing, the escape interval counters within pacer timing/control circuitry 70 are reset upon sensing of P-waves and R-waves as indicated by a signals on lines 62 and 68, and in accordance with the selected mode of pacing on time-out trigger generation of pacing pulses by pacer output circuitry 72 and 74, which are coupled to electrodes 50, 52, 54 and 56. The escape interval counters are also reset on generation of pacing pulses, and thereby control the basic timing of cardiac pacing functions, including anti-tachyarrhythmia pacing. The durations of the intervals defined by the escape interval timers are determined by microprocessor 78, and are supplied via data/address bus 76. The value of the count present in the escape interval counters when reset by sensed R-waves and P-waves may be used to measure the durations of R-R intervals, P-P intervals, P-R intervals and R-P intervals, which measurements are stored in memory 80 and used to detect the presence of tachyarrhythmias.

Microprocessor 78 typically operates as an interrupt-driven device, under control of a stored program in its read only memory and is responsive to interrupts from pacer timing/control circuitry 70 corresponding to the occurrence sensed P-waves and R-waves and corresponding to the generation of cardiac pacing pulses. These interrupts are provided via data/address bus 76. Any necessary mathematical calculations to be performed by microprocessor 78 and any updating of the values or intervals controlled by pacer timing/control circuitry 70 take place following such interrupts.

In one embodiment, microprocessor analyzes the cardiac waveforms sensed by electrodes 50–56 to determine the presence of an arrhythmia. This signals, which are provided by amplifier circuit 86 to analog-to-digital (A/D) circuit 90 and then stored in RAM 80, may be utilized by the microprocessor 78 to determine heart rate and/or arrhythmia type. For example, ventricular tachycardias (VTs) generally are those arrhythmias with rates between 150 and 250 bpm. These rhythms can be further differentiated by their ECG configuration as either monomorphic or polymorphic. Arrhythmias with rates above the upper VT range, and up to approximately 350 bpm, are often termed flutter waves. Chaotic waveforms at rates higher than 350 bpm are classified as ventricular fibrillation (VF).

After the microprocessor has detected an arrhythmia, an appropriate therapy may be selected. In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 78 into pacer timing/control circuitry 70. In the event that generation of a cardioversion or defibrillation pulse is required, microprocessor 78 employs an escape interval counter to control timing of such cardioversion and defibrillation pulses, as well as associated refractory periods.

In response to the detection of atrial or ventricular fibrillation or tachyarrhythmia requiring a cardioversion pulse, microprocessor 78 activates cardioversion/defibrillation control circuitry 92, which initiates charging of high voltage capacitors 108 and 110 via charging circuit 112, under control of high voltage charging control lines 100.

Charging circuit 112 includes circuitry that transfers energy from a power supply, such as a battery, to an energy storage device or devices, such as capacitors 108 and 110. Charging circuit 112 usually comprises a switched circuit with an inductive element such as a transformer. By rapidly opening and closing a control switch, charging circuit 112 transfers energy from the power supply to the inductive element, and from the inductive element to capacitors 108 and 110. As capacitors 108 and 110 store more energy, the voltage across capacitors 108 and 110 increases.

The voltage on high voltage capacitors 108 and 110 is monitored via VCAP line 98, which is passed through multiplexer 88 and in response to reaching a predetermined value set by microprocessor 78, results in generation of a logic signal on Cap Full (CF) line 114, terminating charging.

Once capacitors 108 and 110 are charged, timing of the delivery of the defibrillation or cardioversion pulse is controlled by pacer timing/control circuitry 70. Following delivery of the fibrillation or tachyarrhythmia therapy, the microprocessor then returns the device to cardiac pacing and awaits the next successive interrupt due to pacing or the occurrence of a sensed atrial or ventricular depolarization.

Delivery of the cardioversion or defibrillation pulses is accomplished by output circuit 94, under control of control circuitry 92 via control bus 96. Output circuit 94 determines whether a monophasic or biphasic pulse is delivered, the polarity of the electrodes and which electrodes are involved in delivery of the pulse. Output circuit 94 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in some implantable defibrillators.

Data transmitted to a receiver outside of the patient's body are supplied via data/address bus 76 to telemetry device 118. An external receiver receives the transmitted data, or uplink, and may present the data to medical providers such at the physician treating the patient. The uplink may include, for example, data showing atrial or ventricular electrograms. The data may be useful, and in some cases essential, to the physician in treating the patient. The data may be especially important when the patient is experiencing conditions that may require defibrillation.

In addition to transmitting an uplink, telemetry device 118 may also receive a downlink, i.e., data transmitted to the implanted device. The downlink may include, for example, instructions that program the device to the particular needs of the patient.

As is evident from the above discussion, receiving an accurate cardiac signal via amplifier circuit 86 is essential to appropriate therapy and diagnosis. If a noisy signal is provided by amplifier circuit, microprocessor 78 may erroneously diagnose the presence of an arrhythmia. In response, a painful high-voltage shock may be delivered to the patient when, in fact, no shock was needed. Additionally, oversensing of P and R waves provided on the P-out 62 and R-out 68 signal lines, respectively, may result in the delivery of pacing therapy that is inappropriately timed. Finally, the signal provided to a clinician via telemetry circuit 118 may result in an inaccurate diagnosis of the patient's condition. As a result, inappropriate therapy may be prescribed.

For all of the fore-going reasons, it is important to ensure that the signal generated by the various amplifiers 58, 64, and 86 is as noise-free as possible. This is difficult, however, when a signal is being sensed during the charging of a high-voltage capacitor. This is because electromagnetic emissions from charging circuit 112 can interfere with the operations of the amplifier circuitry. This is particularly problematic when a cardiac waveform is being analyzed to determine whether an arrhythmia has been terminated due to prior-delivered therapy. For example, in some systems, a first response to an arrhythmia involves delivery of anti-tachy pacing (ATP). A painful high-voltage shock is delivered to the patient only after it has been determined that the ATP therapy was unsuccessful. In some systems, the determination as to the effectiveness of the ATP therapy is made while the high-voltage capacitors are charged in preparation for shock delivery. Noise due to the capacitor charging may prevent the detection of the arrhythmia termination, resulting in shock delivery.

As noted above, charging of the high-voltage capacitors result in electromagnetic emissions. This is particularly true when charging circuit 112 includes an inductive element such as a transformer. The current through the inductive element cannot start and stop instantaneously. If this type of abrupt starting and stopping of current flow is attempted, a correspondingly abrupt shift in the potential of the ground plane occurs, causing a noise spike. This noise spike affects signal analysis, as described above. To prevent this, charging of the high-voltage capacitors is initiated and terminated more gradually.

Figure 3:
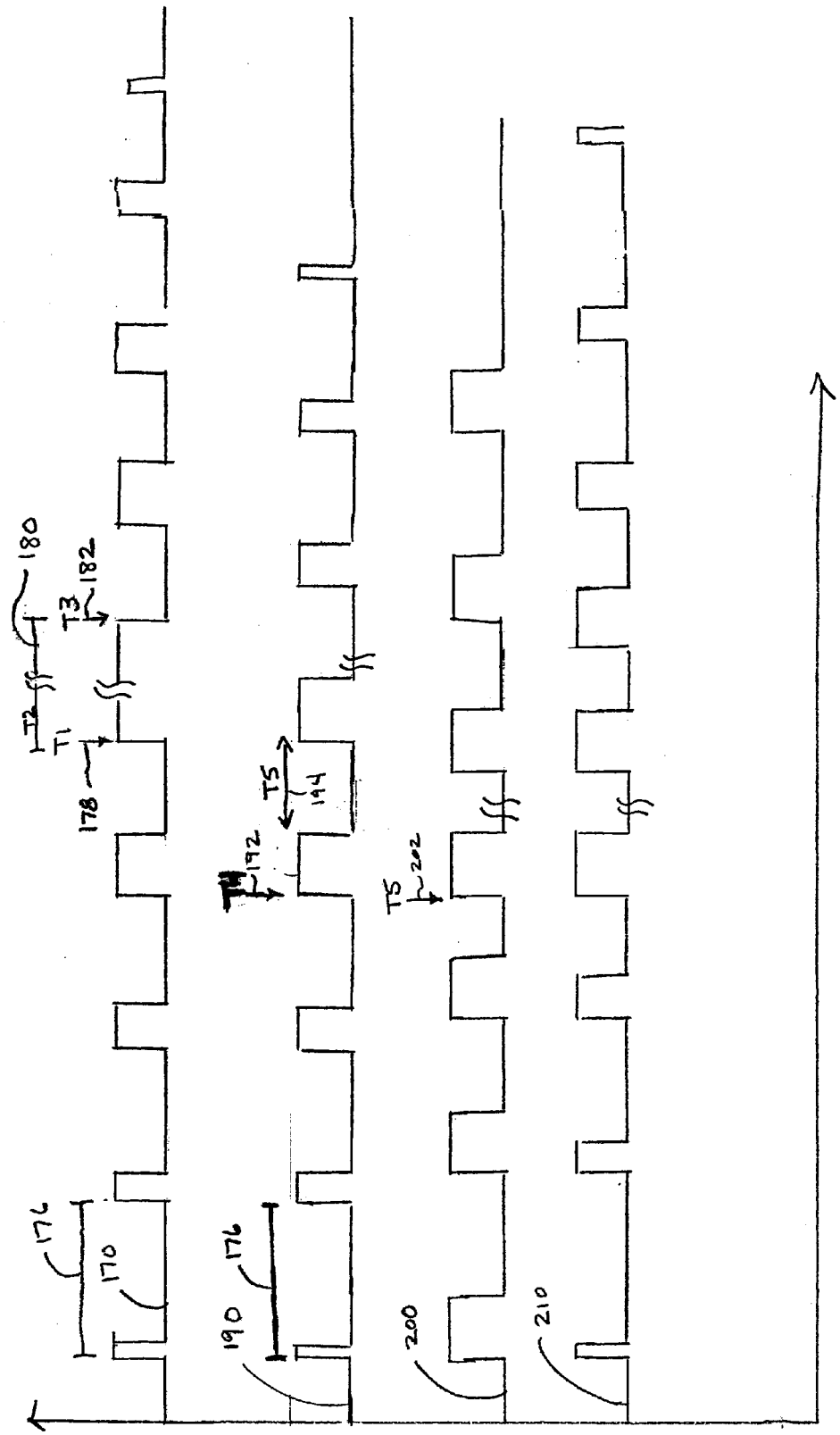
FIG. 3 is a timing diagram illustrating various embodiments of the current invention.

FIG. 3 is a timing diagram illustrating the timing associated with the charge control signal (FIG. 2) in several embodiments of the current invention. This signal opens and closes the control switch in charging circuit 112. For purposes of the current example, it will be assumed the charge control signal is high-active such that charging of the capacitors is enabled when the charge control signal is at a high-active level. In an alternative embodiment, charging could be enabled by a low-active version of this signal. In either embodiment, charge control signal 100 is initially a pulsed signal having a substantially fixed period 176, but a variable duty cycle. The duty cycle gradually increases such that charging of the capacitors is gradually enabled. This avoids the generation of a noise spike, which may adversely affect the ability of the implanted device to accurately detect true cardiac signals. As the duty cycle increases, more energy is transferred to the capacitors with each switching operation, until the maximum charging rate is achieved at time T1 178. Thereafter, charging may be enabled for a predetermined period of time T2 180 as determined by the programmed level of energy to be associated with the shock delivery.

After the maximum energy level on the capacitors has been obtained at time T3 182, charging of the capacitors may be gradually disabled. This is accomplished by gradually decreasing the duty cycle of the charge control signal after time T3. The duty cycle may be reduced by a predetermined amount every period, for example. As the duty cycle decreases, less energy is transferred to the capacitors with each switching operation. Eventually, charging of the capacitors is completely disabled.

As discussed above, the gradual increase and decrease of charging as represented by waveform 170 greatly reduces the amount of ground plane shift that occurs within the circuit, and thereby eliminates noise associated with the amplifiers.

As may be noted in regards to the above-described embodiment, the capacitor charging rate initially increases until the capacitors are being continuously charged. This may not be desirable. In addition to causing noise that may disrupt signal reception by the amplifier circuits, charging of the high-voltage capacitors may also disrupt the operation of other circuitry within the system. For example, telemetry transmissions performed by telemetry circuit 118 can be corrupted by noise generated by charge circuit 112, resulting in data errors. For this reason, it may be desirable to use a pulsed charge control signal 100 that is periodically disabled even after the maximum charge rate has been obtained. This allows telemetry transmissions to occur during the times when capacitor charging is disabled. This is particularly useful in allowing cardiac signals to be transferred from a device while the high-voltage capacitors are charging in preparation to deliver therapy for the arrhythmia. A system and method for performing telemetry transmissions in this manner during charging of high-voltage capacitors is described in detail in patent application Ser. No. 09/947,691 entitled "Controlling Noise Sources During Telemetry" filed on even date herewith, and incorporated herein by reference in its entirety.

Waveform 190 illustrates an alternative embodiment of the current invention. This embodiment is adapted for use in a system such as described in the foregoing paragraph. In a manner similar to that shown in waveform 170, charge control signal 100 has a substantially fixed frequency but a variable duty cycle. The duty cycle gradually increases so that capacitor charging is also gradually increased. After time T4 192, charging occurs at a constant rate as enabled by a pulsed signal that maintains a substantially constant duty cycle and period. Telemetry transmissions may occur when charging is disabled, as during time T5 194. Eventually, capacitor charging is completed, and the charge control signal gradually disables capacitor charging as the duty cycle gradually decreases to zero.

In the embodiment shown in waveform 190, the clock frequency is constant. A typical switching frequency is 100 kHz, which corresponds to a charge control period 176 of 0.01 milliseconds. The clock may generate a noise spectrum, but because the clock has a fixed frequency, the noise spectrum of the clock is known. The clock and amplifier filters may be selected so that the noise generated by the clock does not affect the amplified signals, which allows the noise level to be reduced even further.

An alternative embodiment of the invention is represented by waveform 200. In this embodiment, the frequency of the clock is changed rather than the duty cycle. The clock frequency is increased gradually up to a constant rate at time T5 202, while the pulse width remains substantially constant. Thereafter, the period and duty cycle remain constant in the manner discussed above in reference to waveform 190. After charging is completed, the pulse frequency of the charge control signal may be gradually decreased such that capacitor charging is gradually disabled. It may be noted that in this embodiment, the noise spectrum produced by the clock is not known, making it more difficult to filter the clock noise from the cardiac signal.

Another embodiment of the invention is represented by waveform 210. In this embodiment, both the frequency and duty cycle of the charge control signal 100 are gradually increased upon initiation of the capacitor charging. A similar mechanism may be used to gradually decrease capacitor charging after the energy stored by the capacitors has reached a predetermined level.

Figure 4:
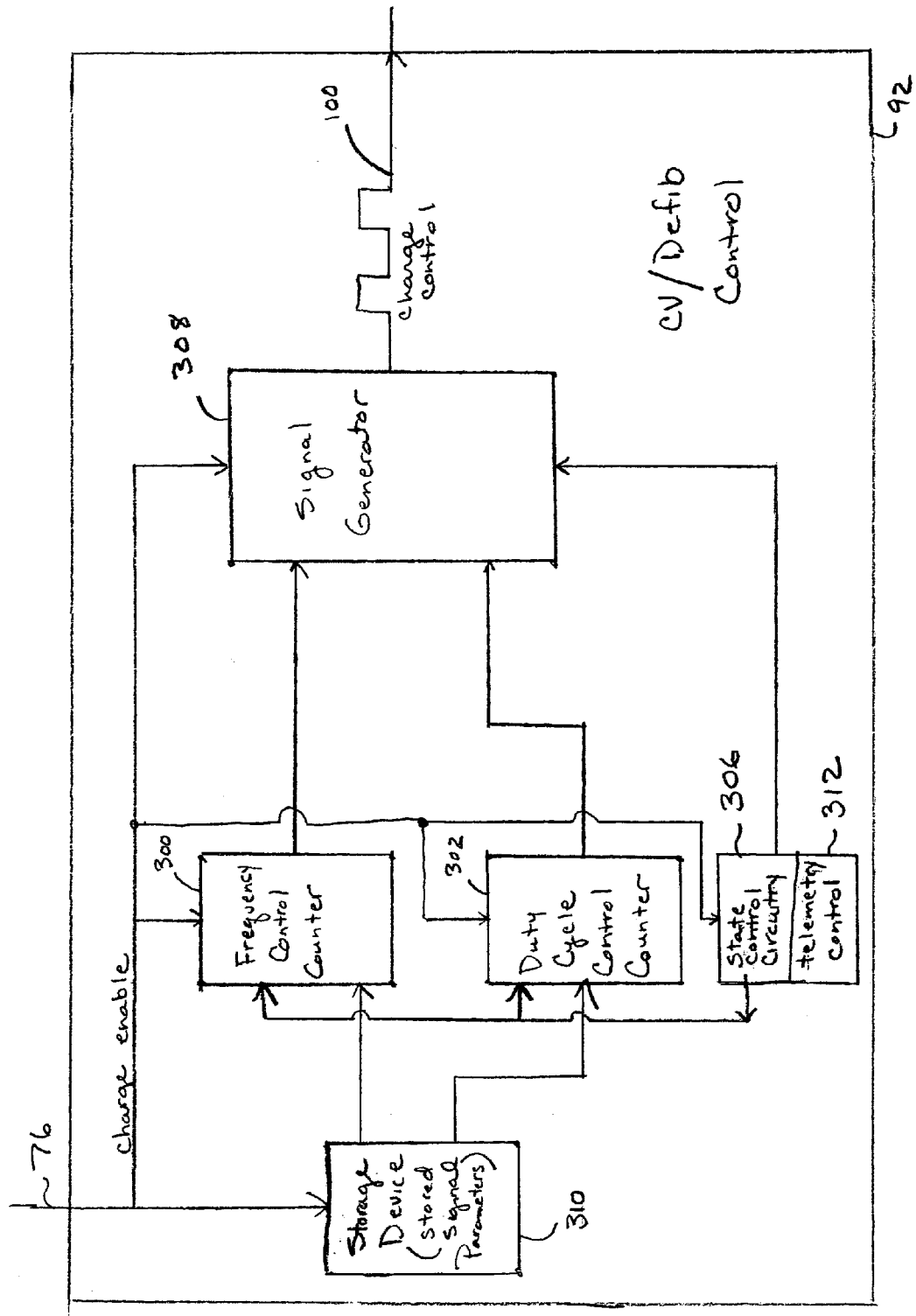
FIG. 4 is one embodiment of a control circuit for use according to the current invention.

FIG. 4 is one embodiment of control circuit 92 according to the current invention. The control circuit receives a signal provided on bus 76 (FIG. 2) that enables charging of the capacitor. This signal may be provided by microprocessor 78, or some other logic circuit after it has been determined that the capacitors are to be charged in preparation for high-voltage shock delivery. This signal is provided to the various logic blocks of the CV/Defib control circuit 92 to initiate the charging operation.

In one embodiment, control circuit 92 includes a frequency control counter 300 and a duty cycle control counter 302. Both are counter/timer circuits that can be incremented and/or decremented by predetermined amounts under the control of state logic 306. The values in these counter/timer circuits are provided to signal generator 308 to control the variable frequency and duty cycle of pulses included in charge control signal 100 that is generated by the signal generator. As discussed above, this signal may include pulses having a variable frequency, variable duty cycle, or both, and is used to enabled charging of the high-voltage capacitors in a gradual manner that does not generate a noise spike.

According to one aspect of the invention, the amount the frequency and/or duty cycle varies per unit time or per pulse period may be programmably selected via signals stored in storage device 310. Other parameters associated with the system may be programmed, such as whether intermittent interruptions are provided after the maximum charge rate has been attained. As discussed above, this may be desirable to provide for telemetry transmission having minimal noise interference. The timing associated with these interruptions is controlled by telemetry control logic 312, which may be a state machine.

It will be understood that the circuit of FIG. 4 is exemplary, and other variations may be utilized. For example, a processor circuit could be substituted for the state logic, or alternatively, control lines generated by microprocessor 78 may be utilized for this control.

In all of the foregoing embodiments of the invention, capacitor charging is gradually increased to a maximum charge rate. When charging has completed as determined by the capacitors reaching a predetermined programmed energy level such as 30 Joules, or when charging is aborted by microprocessor 78, charging is thereafter gradually decreased. In this manner, the occurrence of noise spikes may be greatly reduced, minimizing the chance of P and R wave oversensing, and further minimizing the chance of a misdiagnosed cardiac rhythm. This reduces the possibility of unnecessary shock delivery.

It will be appreciated that the above-described embodiments are exemplary in nature, and other embodiments are possible within the scope of the current invention. For example, the charge control signal could be gradually enabled in a more random manner than that shown in FIG. 3. Alternatively, the charge control signal could be enabled at a faster or slower rate than it is disabled. Moreover, different mechanisms may be used to enable the charge control signal as compared to disabling the signal. For example, the frequency could be varied to gradually enable the signal, whereas the duty cycle could be varied to disable the signal. Therefore, the above description is to be considered exemplary in nature only, with the scope of the invention to be set forth in the following claims.

What is claimed is:

1. An implantable medical device (IMD), comprising:
   a charge storage device;
   a charging circuit coupled to store energy on the charge storage device, the charging circuit having an enabled state and a disabled state; and
   a control circuit coupled to the charging circuit to cause the charging circuit to transition from the disabled state to the enabled state over a first period of time, wherein the control circuit includes a circuit to cause the charging circuit to transition from the enabled state to the disabled state over a second period of time and the control circuit includes a signal generation circuit to generate a pulse train with a variable duty cycle, and wherein the duty cycle of pulses in the pulse train ma be increased over the first period of time to cause the charging circuit to transition from the disabled state to the enabled state.

2. The device of claim 1, wherein the signal generation circuit includes a circuit to decrease the duty cycle of pulses in the pulse train over time to cause the charging circuit to transition from the enabled state to the disabled state during the second period of time.

3. The device of claim 2, wherein the signal generation circuit further includes a circuit to vary the frequency of the pulses in the pulse train over time.

4. The device of claim 1, wherein the charging circuit includes an inductive element.

5. An implantable medical device (IMD), comprising:
   a charge storage device;
   a charging circuit coupled to store energy on the charge storage device, the charging circuit having an enabled state and a disabled state; and
   a control circuit coupled to the charging circuit to cause the charging circuit to transition from the disabled state to the enabled state over a first period of time, wherein the control circuit includes a circuit to cause the charging circuit to transition from the enabled state to the disabled state over a second period of time, wherein the control circuit includes a signal generation circuit to generate a pulse train, and wherein the frequency of pulses in the pulse train may be increased over the first period of time to cause the charging circuit to transition from the disabled state to the enabled state.

6. The device of claim 5, wherein the signal generation circuit includes a circuit to decrease the frequency of the pulses in the pulse train over the second period of time to cause the charging circuit to transition from the enabled state to the disabled state.

7. An implantable medical device (IMD), comprising:
   a charge storage device;
   a charging circuit coupled to store energy on the charge storage device, the charging circuit having an enabled state and a disabled state; and
   a control circuit coupled to the charging circuit to cause the charging circuit to transition from the disabled state to the enabled state over a first period of time, wherein the control circuit includes a circuit to cause the charging circuit to transition from the enabled state to the disabled state over a second period of time, and further including a telemetry circuit in proximity to the charging circuit, and wherein the control circuit further includes a circuit to temporarily interrupt a charging operation for a predetermined period of time when the charging circuit is in the enabled state, and to thereafter enable a transmission between the telemetry circuit and a device external to the IMD while the charging operation is temporarily interrupted.

8. An implantable medical device (IMD), comprising:

a charge storage device;

a charging circuit coupled to store energy on the charge storage device, the charging circuit having an enabled state and a disabled state; and a control circuit coupled to the charging circuit to cause the charging circuit to transition from the disabled state to the enabled state over a first period of time, wherein the control circuit includes a circuit to cause the charging circuit to transition from the enabled state to the disabled state over a second period of time, wherein the charge storage device is a high-voltage capacitor.

9. An implantable medical device (IMD), comprising:

an energy storage device;

a charging circuit coupled to store charge on the energy storage device; and a control circuit coupled to the charging circuit, the control circuit to cause the charging circuit to store charge at a varying charge rate, wherein the control circuit includes a circuit to cause the charging circuit to increase the charge rate from a rate wherein substantially no charge is being stored to a second predetermined rate and the control circuit includes a circuit to cause the charging circuit to decrease the charge rate from the second predetermined rate to the rate wherein substantially no charge is being stored, and wherein the control circuit includes a signal generation circuit that generates a pulse train having a variable duty cycle.

10. The IMD of claim 9, wherein the signal generation circuit includes a circuit to vary the frequency of the pulse train.

11. An implantable medical device (IMD), comprising:

a storage device;

a charging circuit coupled to store charge on the energy storage device; and a control circuit coupled to the charging circuit, the control circuit to cause the charging circuit to store charge at a varying charge rate, wherein the control circuit includes a circuit to cause the charging circuit to increase the charge rate from a rate wherein substantially no charge is being stored to a second predetermined rate and the control circuit includes a circuit to cause the charging circuit to decrease the charge rate from the second predetermined rate to the rate wherein substantially no charge is being stored, and wherein the control circuit includes a signal generation circuit that generates a pulse train having a variable frequency.

12. An implantable medical device (IMD), comprising:

an energy storage device;

a charging circuit coupled to store charge on the energy storage device;

a control circuit coupled to the charging circuit, the control circuit to cause the charging circuit to store charge at a varying charge rate; and a communication circuit coupled to the charge circuit, wherein the control circuit includes a circuit to cause the charging circuit to increase the charge rate from a rate wherein substantially no charge is being stored to a second predetermined rate and the control circuit includes a circuit to cause the charging circuit to decrease the charge rate from the second predetermined rate to the rate wherein substantially no charge is being stored, and wherein the control circuit includes a circuit to temporarily interrupt charging of the charge circuit to allow the communication circuit to transmit data to an external device.

13. A method for use in an implantable medical device (IMD), the IMD including a ground plane and a charge storage device, the method comprising the steps of:

a.) initiating storing of a charge on the charge storage device; and b.) controlling the rate of the storing of the charge in a manner that maintains the ground plane of the IMD at a substantially constant voltage potential.

14. The method of claim 13, wherein step b.) includes increasing the rate of the storing of the charge from a state wherein substantially no charge is being stored to a second rate.

15. The method of claim 14, and further including the step of decreasing the rate of the storing of the charge from the second rate to the state wherein substantially no charge is being stored.

16. The method of claim 15, wherein step b.) includes utilizing a signal including a pulse train, and wherein at least some of the pulses in the pulse train have a variable duty cycle to control the rate of change.

17. The method of claim 16, wherein step b.) includes utilizing a signal including a pulse train, and wherein at least some of the pulses in the pulse train have a variable frequency to control the rate of change.

18. The method of claim 16 or 17, and further including:

interrupt the storing of the charge temporarily; and performing a communication operation between the IMD and an external device during the interruption of the storing of the charge.

19. An implantable medical device, comprising:

means for storing a charge;

means for initiating storing of a charge on the charging means; and means for controlling the rate of the storing of the charge in a manner that maintains a ground plane of the device at a substantially constant voltage potential.

20. The device of claim 19, further comprising means for increasing the rate of the storing of the charge from a state wherein substantially no charge is being stored to a second rate.

21. The device of claim 20, further comprising means for decreasing the rate of the storing of the charge from the second rate to the state wherein substantially no charge is being stored.

22. The device of claim 21, wherein the means for controlling the rate of the storing utilizes a signal including a pulse train, and wherein at least some of the pulses in the pulse train have a variable duty cycle to control the rate of change.

23. The device of claim 22, wherein at least some of the pulses in the pulse train have a variable frequency to control the rate of change.

24. The device of claim 23, further comprising:

means for interrupt the storing of the charge temporarily; and means for performing a communication operation between the device and an external device during the interruption of the storing of the charge.

25. The device of claim 22, further comprising:

means for interrupting the storing of the charge temporarily; and means for performing a communication operation between the device and an external device during the interruption of the storing of the charge.

* * * * *

UNITED STATES PATENT AND TRADEMARK OFFICE
CERTIFICATE OF CORRECTION

PATENT NO.    : 6,754,527 B2
DATED         : June 22, 2004
INVENTOR(S)   : John C. Stroebel et al.

It is certified that error appears in the above-identified patent and that said Letters Patent is hereby corrected as shown below:

Column 10,
Line 22, delete "train ma be", replace with -- train may be --.

Column 11,
Line 37, delete "a storage", replace with -- an energy storage --.

Column 12,
Line 55, delete "for interrupt", replace with -- for interrupting --.

Signed and Sealed this

Eleventh Day of January, 2005

JON W. DUDAS
*Director of the United States Patent and Trademark Office*